US009797835B2

United States Patent
Sun et al.

(10) Patent No.: US 9,797,835 B2
(45) Date of Patent: Oct. 24, 2017

(54) IN-SITU ON-LINE DETECTION DEVICE AND METHOD FOR LONG-DISTANCE METALLURGICAL LIQUID METAL COMPONENT

(71) Applicant: SHENYANG INSTITUTE OF AUTOMATION OF THE CHINESE ACADEMY OF SCIENCES, Liaoning (CN)

(72) Inventors: Lanxiang Sun, Liaoning (CN); Haibin Yu, Liaoning (CN); Yong Xin, Liaoning (CN); Lifeng Qi, Liaoning (CN); Yang Li, Liaoning (CN); Zhibo Cong, Liaoning (CN)

(73) Assignee: SHENYANG INSTITUTE OF AUTOMATION OF THE CHINESE ACADEMY OF SCIENCES, Liaoning (CN)

( * ) Notice: Subject to any disclaimer, the term of this patent is extended or adjusted under 35 U.S.C. 154(b) by 0 days.

(21) Appl. No.: 14/898,600

(22) PCT Filed: Nov. 28, 2013

(86) PCT No.: PCT/CN2013/087988
§ 371 (c)(1),
(2) Date: Dec. 15, 2015

(87) PCT Pub. No.: WO2015/007041
PCT Pub. Date: Jan. 22, 2015

(65) Prior Publication Data
US 2016/0131581 A1     May 12, 2016

(30) Foreign Application Priority Data
Jul. 15, 2013   (CN) .......................... 2013 1 0303439

(51) Int. Cl.
*G01N 21/63*   (2006.01)
*G01N 21/71*   (2006.01)
(Continued)

(52) U.S. Cl.
CPC ............. *G01N 21/63* (2013.01); *G01B 11/14* (2013.01); *G01N 21/21* (2013.01); *G01N 21/718* (2013.01);
(Continued)

(58) Field of Classification Search
CPC ...... G01N 21/63; G01N 21/21; G01N 33/206; G01N 21/718; G01N 21/8507;
(Continued)

(56) References Cited

U.S. PATENT DOCUMENTS 4,561,777 A * 12/1985 Radziemski ....... G01N 15/0618
356/318
4,798,428 A *  1/1989 Karim .................... G02B 6/32
385/74
(Continued)

FOREIGN PATENT DOCUMENTS

CA   WO 2014121389 A1 *  8/2014  ............ G01J 3/0243
CN       201732059 U       2/2011
(Continued)

OTHER PUBLICATIONS https://marketplace.idexop.com/store/SupportDocuments/TNH_HTB_Polarizers.pdf.*
(Continued)

*Primary Examiner* — Tarifur Chowdhury
*Assistant Examiner* — Mohamed K Amara
(74) *Attorney, Agent, or Firm* — Smith, Gambrell & Russell, LLP (57) ABSTRACT

An in-situ on-line detection device and detection method for a long-distance metallurgical liquid metal component. The
(Continued)

detection device comprises a front-end high-temperature resistant probe, a middle-end optical sensing device and a back-end control platform, wherein the head of the front-end high-temperature resistant probe is placed in a liquid metal, the tail thereof is coaxially connected to the middle-end optical sensing device, and an optical window is arranged in the connection position; and the middle-end optical sensing device is connected to the back-end control platform through a signal line. The detection device and detection method can provide a timely and valid message for quality control and a melting end, so that the detection time is greatly shortened, the detection distance can he adjusted extensively, the measurement result is accurate, and it can be achieved to measure components that are difficult to measure such as carbon, sulfur, phosphorous, etc.

15 Claims, 4 Drawing Sheets

(51) Int. Cl.
  *G01N 21/85* (2006.01)
  *G01B 11/14* (2006.01)
  *G01N 21/21* (2006.01)
  *G01N 33/20* (2006.01)
  *G01N 21/69* (2006.01)

(52) U.S. Cl.
  CPC ....... *G01N 21/8507* (2013.01); *G01N 33/206* (2013.01); *G01N 2021/695* (2013.01); *G01N 2201/0636* (2013.01); *G01N 2201/0683* (2013.01); *G01N 2201/06113* (2013.01); *G01N 2201/088* (2013.01)

(58) Field of Classification Search
  CPC . G01N 2201/06113; G01N 2201/0683; G01N 2201/0636; G01N 2201/088; G01N 2021/695; G01B 11/14
  See application file for complete search history.

(56) References Cited

U.S. PATENT DOCUMENTS

| | | | | |
|---|---|---|---|---|
| 4,925,307 A * | 5/1990 | Cremers | ............... | G01N 21/718 356/318 |
| 4,986,658 A * | 1/1991 | Kim | ........................ | G01J 3/02 148/508 |
| 4,995,723 A * | 2/1991 | Carlhoff | ..................... | G01J 3/02 356/318 |
| 5,751,416 A * | 5/1998 | Singh | ........................ | G01J 3/30 356/300 |
| 5,946,089 A * | 8/1999 | Duer | ..................... | G01N 21/718 356/318 |
| 6,396,069 B1 * | 5/2002 | MacPherson | ...... | G01B 11/2441 250/559.22 |
| 6,532,068 B2 * | 3/2003 | Detalle | ................ | B23K 26/032 219/121.76 |
| 6,940,888 B2 * | 9/2005 | Liu | ........................ | H01S 3/081 356/28 |
| 7,092,087 B2 * | 8/2006 | Kumar | ................. | A61B 5/0075 250/461.2 |
| 7,106,439 B2 * | 9/2006 | Lacour | ................. | G01N 21/718 356/318 |
| 7,876,803 B1 * | 1/2011 | Di Teodoro | ........ | H01S 3/06791 372/10 |
| 2003/0081180 A1 * | 5/2003 | Suzuki | ................. | H04N 9/3105 353/31 |
| 2003/0174325 A1 | 9/2003 | Zhang et al. | | |
| 2003/0234928 A1 | 12/2003 | Lucas et al. | | |
| 2008/0212074 A1 * | 9/2008 | Goulter | ..................... | G01J 3/02 356/51 |
| 2009/0237783 A1 * | 9/2009 | Kim | ........................ | G02B 23/02 359/407 |
| 2011/0218403 A1 * | 9/2011 | Tearney | ............... | A61B 5/0066 600/165 |
| 2012/0057145 A1 * | 3/2012 | Tunnell | ................... | G01N 21/31 356/51 |
| 2012/0314214 A1 * | 12/2012 | Alexander | ............. | G01J 3/443 356/318 |
| 2013/0038877 A1 * | 2/2013 | Nelson | ...................... | G01J 3/02 356/417 |
| 2013/0135978 A1 * | 5/2013 | Ide | ........................ | G11B 7/0917 369/53.28 |
| 2014/0176940 A1 * | 6/2014 | Fishbine | ............... | G01J 3/0218 356/301 |
| 2015/0103334 A1 * | 4/2015 | Quant | .................. | G01N 21/718 356/51 |

FOREIGN PATENT DOCUMENTS

| | | | | |
|---|---|---|---|---|
| CN | 102305785 A | | 1/2012 | |
| CN | 102507512 A | | 6/2012 | |
| CN | 102841075 A | | 12/2012 | |
| DE | 102013021222 A1 * | 6/2015 | ......... | G01N 21/6458 |
| FR | EP 1640706 A1 * | 3/2006 | ........... | G01N 21/211 |
| GB | WO 2011117589 A1 * | 9/2011 | ............. | G01N 15/14 |
| JP | DE 102010000467 A1 * | 12/2010 | ......... | G01B 11/0608 |
| WO | WO 2010123530 A1 * | 10/2010 | ........... | G01N 21/718 |

OTHER PUBLICATIONS https://en.wikipedia.org/wiki/Achromatic_lens.*
Google Translation of CN102305785 to Sun et al.*
International Search Report for PCT/CN2013/087988, dated Apr. 22, 2014 in English & Chinese Language.
Mathy, G. Monfort, B. Vanderheyden, V. Tusset, Measurement of composition and temperature in blast furnace runners by using laser induced breakdown spectroscopy. Metall. Anal. 2011,31(10):21-23.
Reinhard Noll, Laser-Induced Breakdown Spectroscopy: Fundamentals and Applications, Springer 2012. 1-543.
Lin Xiaomei, Cao Jiqing, Yin Qinghui, and Liu Xiaoqing, Online Analysis of Silicone Content in AOD Furnace Based on LIBS, Magnesium Alloy, 2009 (1): 41-44.
Robert De Saro, Arel Weisberg, and Joe Craparo, In Situ, Real Time Measurement of Aluminum, Steel, and Glass Melt Chemistries Using Laser Induced Breakdown Spectroscopy, 2005 ACEEE Summer Study on Energy Efficiency in Industry 2005. 1-25 to 1-35.
Mohamed A. Khater, Laser-induced breakdown spectroscopy for light elements detection in steel: State of the art, Spectrochimica Acta Part B 81 (2013) 1-10.
Written Opinion of the International Searching Authority for PCT/CN/087988 dated Jan. 15, 2016 (Chinese with English Translation—14 pages).

* cited by examiner

IN-SITU ON-LINE DETECTION DEVICE AND METHOD FOR LONG-DISTANCE METALLURGICAL LIQUID METAL COMPONENT

TECHNICAL FIELD

The present invention relates to the technical field of long-distance online monitoring for high-temperature liquid component, in particular to an in-situ online detection device and method for long-distance metallurgical liquid metal component.

BACKGROUND

In the melting processes of metal and alloy, the change of chemical component is required to be detected, so as to control the product quality and judge a melting end. At present, due to the lack of an advanced and effective online measurement technology, the offline detection manner of manual sampling and sample preparation is generally adopted in the melting processes. For example, during the steel melting process, in the detection of high-temperature molten steel, the molten steel is required to be taken onto an analytical instrument for measurement and analysis after a series of processes of sampling, cooling, grinding, polishing, etc., and it needs to take 3 to 5 minutes in the entire process that will occupy more than one tenth of melting time. This time-consuming offline detection manner not only causes backward quality control, but also causes the waste of large amount of resources and energy resources. Moreover, detection equipment is expensive, bulky and difficult to adapt to modern melting production requirements.

A Laser Induced Breakdown Spectroscopy (LIBS) is a technology of using laser for exciting plasma and then using the emission spectra of the plasma for performing element detection and analysis. It does not need a complicated sample pretreatment process, has not strict requirements for the appearance and the size of samples, has low consumption quantity of the samples, is suitable for solid, liquid and gas simultaneously and can be used for performing simultaneous determination on multiple elements. Therefore, this technology presents an excellent application value in the aspects of in-situ, online, quick and remote analysis.

With the increasing enlargement, high speed and continuity of the production mode of metallurgical industry, there is an increasingly urgent demand for an in-situ online detection technology for liquid metal component, and an online detection device based on the Laser Induced Breakdown Spectroscopy (LIBS) begins to appear.

The literature (Reinhard Noll, Laser-Induced Breakdown Spectroscopy: Fundamentals and Applications, Springer 2012) presents the research status of detection equipment by using LIBS currently. Analytical equipment applied to metal component mainly includes short-distance laboratory equipment. The short-distance laboratory equipment is accurate in measurement and short in time required (tens of seconds), but has enormous volume and higher requirement for the environment, so it cannot better adapt to the online monitoring of complex environments, such as steel factory, etc.

The literature (Lin Xiaomei, Cao Jiqing, Yin Qinghui, and Liu Xiaoqing, Online Analysis of Silicone Content in AOD Furnace Based on LIBS, Magnesium Alloy, 2009 (1): 41-44) presents a device for detecting the content of Si element in an AOD furnace by using LIBS. The device uses a self-design sampler for sampling in the furnace. After that, component detection is performed in a sample pool of the device. The device has shorter detection distance and relatively complicated structural design, can only measure a single element and cannot simultaneously measure multiple elements.

The literature (G Mathy, B. Monfort, B. Vanderheyden, V. Tusset, Liquid steel process: advanced on line sensors under development at CRM. Metall. Anal. 30 (Suppl.1), 6-14 (2010)) presents a TeleLis system for realizing long-distance LIBS detection by using a Newtonian telescope system. The TeleLis system can realize the analysis of element component on a required measuring sample within the range of 3 to 12 meters. However, because a front optical path thereof is an open structure, an ambient environment and air will influence spectrum accuracy. Moreover, the character spectral lines of elements such as C, S, P, etc. are in an ultraviolet region. Air component in the open optical path absorbs these elements strongly, so these character elements cannot be measured.

The literature (Robert De Saro, Arel Weisberg, and Joe Craparo, In Situ, Real Time Measurement of Aluminum, Steel, and Glass Melt Chemistries Using Laser Induced Breakdown Spectroscopy, 2005 ACEEE Summer Study on Energy Efficiency in Industry 2005) reports a device for online measurement of elements such as Al, Cu, Fe, Mn, etc. in an aluminum alloy solution in industrial situ. A probe is inserted into a furnace body for directly measuring a metal solution surface. However, an optical structure is contained inside the probe of the device, and needs to be protected. The probe has a complicated structure.

The literature (Mohamed A. Khater, Laser-induced breakdown spectroscopy for light elements detection in steel: State of the art, Spectrochimica Acta Part B 81 (2013) 1-10) presents the monitoring situation of light elements by using LIBS in metal melting. Because the character spectra of the light elements mainly focus on an ultraviolet region and a deep ultraviolet region, the current major method is to generate an inert gas environment or a vacuum environment for performing measurement, while special gas environments of optical paths are relatively shorter and cannot better adapt to the severe environment of a factory.

In summary, there is currently no complete set of online monitoring equipment for simultaneous measurement of multiple elements (nonmetal elements such as C, S, P, etc.) based on LIBS capable of well adapting to the severe environment of a steel melting factory and having simple structure, strong applicability and lower manufacturing cost and maintenance cost. The existing equipment has different limits in the aspects of structural complexity, environmental need, measurable need, etc., and has relatively narrow application scope.

SUMMARY OF THE PRESENT INVENTION

With respect to the defects in the prior art, the present invention provides an in-situ online detection device and method for metallurgical liquid metal component to provide timely and valid information for the quality control and a melting end, so that the detection time is greatly shortened, the detection distance can be adjusted extensively, the detection device can be flexibly installed and used, the product quality can be greatly improved, the production cost is decreased and the energy consumption is reduced; moreover, a double-pulse method is applied, thereby effectively increasing the spectral quality, suppressing the noise and enhancing the accuracy and the stability of a measurement result; and the measurement on components, such as C, S, P, etc. that are difficult to measure can be achieved.

To realize the above-mentioned purposes, the present invention discloses the technical solution:

An in-situ online detection device for a long-distance metallurgical liquid metal component, wherein:

the head of a front-end high-temperature resistant probe (18) is placed in liquid metal (22), the tail thereof is coaxially connected to a middle-end optical sensing device (19), and an optical window (15) is arranged in the connection position; and the middle-end optical sensing device (19) is connected to a back-end control platform (24) through a signal line (25).

Preferably, in said middle-end optical sensing device (19), a remote beam expanding and focusing module (7) is arranged coaxially in the axis direction in which a laser generating module (6) emits laser beams.

A first reflecting mirror (9) is arranged on the optical axis of the emergent direction of the remote beam expanding and focusing module (7) and forms an angle of 45° with the optical axis thereof; a second reflecting mirror (10) is arranged on the optical axis of the incident direction of a remote signal collecting module (11) and forms an angle of 45° with the optical axis thereof; and a connecting line of the centers of the first reflecting mirror (9) and the second reflecting mirror (10) is perpendicular to the axes of the remote beam expanding and focusing module (7) and the remote signal collecting module (11).

A light splitting piece (20) and an optical fiber coupling module (13) are respectively arranged on the optical axis of the emergent direction of the remote signal collecting module (11); the optical fiber coupling module (13) is connected with an optical fiber spectrometer (14) through an optical fiber (21); and the fiber spectrometer (14) is connected with a back-end control platform (24) through a signal line (25); and a real-time imaging module (12) is vertically arranged on the optical axis of the reflecting direction of the light splitting piece (20), and is connected with the back-end control platform (24) through the signal line (25).

Preferably, said front-end high-temperature resistant probe (18) is an inverted cone in which inert gas is charged so that the optical paths of excitation laser beams and collected plasma signal light are in a closed inert gas environment.

Preferably, said back-end control platform (24) comprises a laser power supply and control unit (1), a time synchronization controller (2), an air inlet control unit (3) and a displacement platform control unit (4), wherein the above-mentioned units are connected with the middle-end optical sensing device (19) through the signal line (25).

Preferably, the in-situ online detection device for the long-distance metallurgical liquid metal component further comprises a laser distance measuring module (8) which is arranged in the direction of the connecting line of the centers of the first reflecting mirror (9) and the second reflecting mirror (10) and the laser distance measuring module (8) is connected with the back-end control platform (24) through the signal line (25).

Preferably, said middle-end optical sensing device (19) further comprises a temperature control module (5) and is connected with the back-end control platform (24) through the signal line (25); and said temperature control module (5) comprises a temperature sensor and a temperature adjusting device for real-time monitoring and adjustment of the internal temperature of the middle-end optical sensing device (19).

Preferably, said laser generating module (6) comprises two groups of laser heads, half-wave plates and polarizing light splitting pieces;

said half-wave plates are coaxially arranged on the optical axes of the laser emergent directions of the laser heads and are perpendicular to the optical axes; and said polarizing light splitting pieces are coaxially arranged on the optical axes of the emergent directions of the half-wave plates and form Brewster's angles with the optical axes, and the second polarizing light splitting piece (31) can receive the laser beams reflected by the first polarizing light splitting piece (30).

Preferably, said remote beam expanding and focusing module (7) comprises a first movable base (32) and a diverging lens and a converging lens which are coaxially arranged in the emergent direction of the laser generating module (6);

said first movable base (32) can move on the optical axis of the emergent direction of the laser generating module (6);

said diverging lens is arranged in the first movable base (32) perpendicularly to the optical axis; and said converging lens is arranged between the first movable base (32) and the first reflecting mirror (9) perpendicularly to the optical axis.

Preferably, said remote signal collecting module (11) consists of a second movable base (37), a hyperboloidal reflecting mirror (38) and a paraboloidal reflecting mirror (39) and is connected with the back-end control platform (24) through the signal line (25);

said second movable base (32) can move on the optical axis of the emergent direction of the second reflecting mirror (10);

said hyperboloidal reflecting mirror (38) is parallel to and coaxial with the emergent direction of the second reflecting mirror (10), and is arranged in the second movable base (37); and said paraboloidal reflecting mirror (39) is arranged between the hyperboloidal reflecting mirror (38) and the light splitting piece, and a central hole is reserved in the center.

Preferably, said remote signal collecting module (11) consists of a second movable base (37), a spherical reflecting mirror and an aspherical reflecting mirror and is connected with the back-end control platform (24) through the signal line (25);

said second movable base (37) can move on the optical axis of the emergent direction of the second reflecting mirror (10);

said spherical reflecting mirror is parallel to and coaxial with the emergent direction of the second reflecting mirror (10), and is arranged in the second movable base (37); and said aspherical reflecting mirror is arranged between the spherical reflecting mirror and the light splitting piece, and a central hole is reserved in the center.

Preferably, said optical fiber coupling module (13) comprises a third diverging lens (40), a third converging lens (41) and a fourth converging lens (42) which are coaxially placed in parallel in sequence, and the optical axis thereof coincides with the optical axis of the remote signal collecting module.

Preferably, said real-time imaging module (12) comprises an achromatic lens (43) and a CCD (44); and the achromatic lens (43) and the CCD (44) are coaxially placed; the axis direction thereof is perpendicular to the direction of the optical axis of the remote signal collecting module (11); and the axis passes through the center of the light splitting piece (20).

An in-situ online detection method for a long-distance metallurgical liquid metal component comprises the following steps:

placing the head of the front-end high-temperature resistant probe (18) in liquid metal (22); and charging inert gas through the air inlet pipe (16) of the high-temperature resistant probe to form a closed inert gas environment;

emitting distance measuring laser by the laser distance measuring module (8); after the distance measuring laser passes through the first reflecting mirror (9) and the second reflecting mirror (10), irradiating the distance measuring laser on a liquid metal surface (23); measuring the position information of the liquid metal surface (23); and feeding the same back to the back-end control platform (24);

performing focusing adjustment on the first movable base (32) and the second movable base (37) by the back-end control platform (24) through the position information of the liquid metal surface (23) fed back by the laser distance measuring module (8) so that the focal position, on which the laser focuses, for exciting the plasma and the collection position of remote signals coincide on the liquid metal surface (23);

receiving a laser generating signal of the back-end control platform (24) by the laser generating module (6); emitting laser beams; after the laser beams pass through the remote beam expanding and focusing module (7), irradiating the laser beams on the first reflecting mirror (9); enabling the reflected laser beams to pass through the second reflecting mirror (10); and irradiating the laser beams to the liquid metal surface (23) through the inert gas environment of the front-end high-temperature resistant probe (18) to produce plasma signal light;

transmitting the generated plasma signal light to the remote signal collecting module (11) through the inert gas environment of the front-end high-temperature resistant probe (18); forming parallel plasma signal light through the paraboloidal reflecting mirror (39) and the hyperboloidal reflecting mirror (38) in the remote signal collecting module (11); and transmitting the same to the optical fiber coupling module (13) through the light splitting piece (20); and after the parallel plasma signal light passes through the optical fiber coupling module (13), transmitting the parallel plasma signal light to the optical fiber spectrometer (14) through the optical fiber (21) for performing light signal collection and photoelectric conversion; and feeding the same back to the back-end control platform (24) to finish the collection of the plasma signal light.

Preferably, the in-situ online detection method for the long-distance metallurgical liquid metal component according to claim 13 further comprises the real-time imaging module (12) which receives a part of signal light and scene background light reflected by the light splitting piece (20), feeds the same back to the back-end control platform (24), displays the appearance of the liquid metal surface (23) and the formation condition of the plasma in real time, and adjusts the focusing position and the collection position in real time.

The present invention has the following beneficial effects and advantages:

Sampling and sample preparation are not required, and high-temperature melt metal component is subject to in-situ online detection, thereby greatly shortening the detection time, providing real-time information for the metallurgical production process, greatly improving the product quality, reducing the production cost and reducing the energy consumption.

A plug-in high-temperature resistant probe is adopted, thereby avoiding the influence of impurities of cinder on a melt surface, etc. on measurement, enabling the measurement result to actually reflect the state of a measured substance and ensuring an accurate result.

The high-temperature resistant probe has simple structure and does not have other optical structures internally; the design and manufacturing cost is relatively low; and different lengths of high-temperature resistant probes can be replaced according to different needs.

The measurement on components, such as C, S, P, etc. that are difficult to measure can be achieved through the transmission of an optical path in an inert gas environment.

The measurement distance can be changed according to the length of the selected high-temperature resistant probe; detection at a distance of 1.5 to 10 meters or above can be realized; and the prevent invention can be flexibly applied to different environmental conditions.

Through the beam combination manner of double pulses, the plasma excitation of double-pulse laser on the samples is realized, thereby enhancing the intensity of plasma signals and reducing the noise; and relative to a single-pulse excitation manner, the detection precision and stability can be greatly enhanced.

The present invention has wide scope of application, and not only can be applied to the measurement of metallurgical melt metal, but also can be suitable for the measurement of other ordinary liquid as well as the measurement of gas and solid substances.

If the high-temperature resistant probe is disassembled, the present invention can be used as a long-distance element online analytical instrument, and can realize long-distance detection of 1.5 to 10 meters or above.

Wherein 1 is a laser power supply and control unit; 2 is a time synchronization controller; 3 is an air inlet control unit; 4 is a displacement platform control unit; 5 is a temperature control unit; 6 is a laser generating module; 7 is a remote beam expanding and focusing module; 8 is a laser distance measuring module; 9 is a first reflecting mirror; 10 is a second reflecting mirror; 11 is a remote signal collecting module; 12 is a real-time imaging module; 13 is an optical fiber coupling module; 14 is an optical fiber spectrometer; 15 is an optical window; 16 is an air inlet pipe of a high-temperature resistant probe; 17 is an air outlet pipe of a high-temperature resistant probe; 18 is a high-temperature resistant probe; 19 is a middle-end optical sensing device; 20 is a light splitting piece; 21 is an optical fiber; 22 is liquid metal; 23 is a liquid metal surface; 24 is a back-end control platform; 25 is a signal line; 26 is a first laser head; 27 is a second laser head; 28 is a first half-wave plate; 29 is a second half-wave plate; 30 is a first polarizing light splitting piece; 31 is a second polarizing light splitting piece; 32 is a first movable base; 33 is a first diverging lens; 34 is a second diverging lens; 35 is a first converging lens; 36 is a second converging lens; 37 is a second movable base; 38 is a hyperboloidal reflecting mirror; 39 is a paraboloidal reflecting mirror; 40 is a third diverging lens; 41 is a third converging lens; 42 is a fourth converging lens; 43 is an achromatic lens; and 44 is a CCD.

DETAILED DESCRIPTION OF THE EMBODIMENTS

The present patent will be further described below in combination with the drawings and the embodiments.

Figure 1:
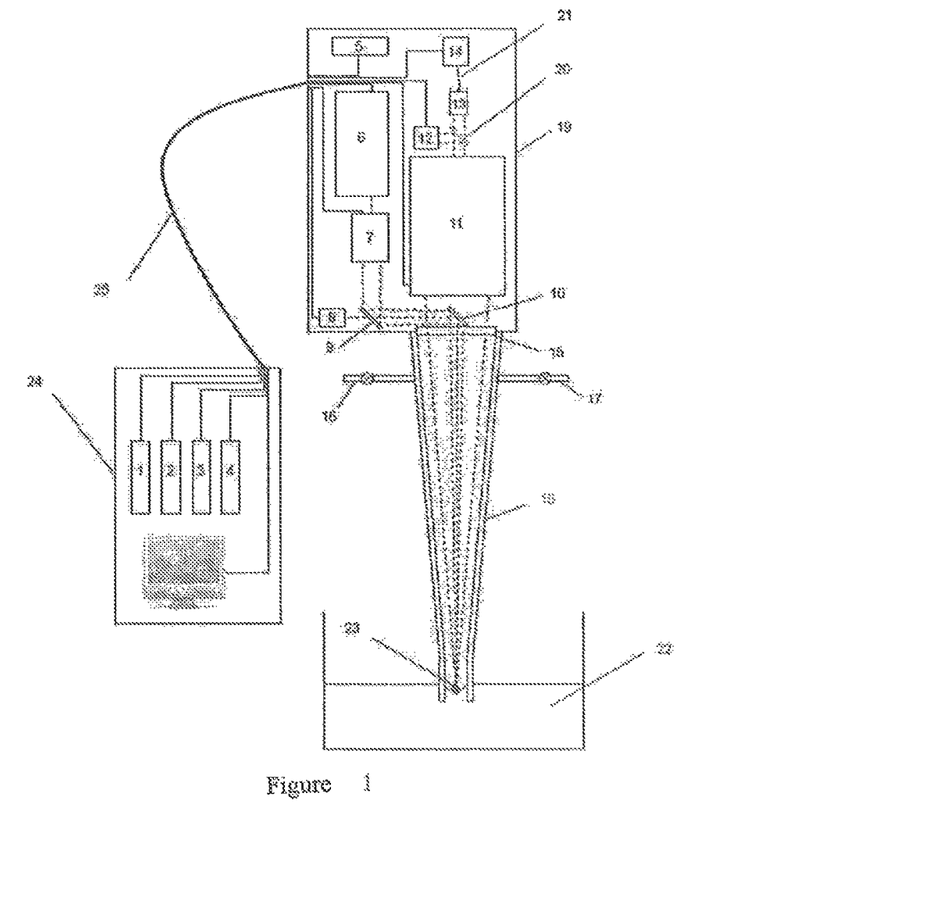
FIG. 1 is an overall structural diagram of the present invention.

FIG. 1 shows an overall structural diagram of the present invention which comprises a front-end high-temperature resistant optical probe 18, a middle-end optical sensing device 19 and a back-end control platform 24, wherein:

The head of the front-end high-temperature resistant probe 18 is placed in metallurgical liquid metal 22; a sealed cavity body is formed internally; and inert gas is charged through the air pipe 16 to form an optical path environment of the inert gas; the middle-end optical sensing device 19 receives an operating signal of the back-end control platform 24; firstly, a distance from the metallurgical liquid metal surface 23 is measured through a laser distance measuring part 8; the first movable base 32 and the second movable base 37 in the remote beam expanding and focusing module 7 and the remote signal collecting module 11 are adjusted according to a feedback signal so that detection laser focuses on the liquid metal surface 23; signal collecting points are in the same position; the laser receives a triggering signal of the back-end control platform for generating the detection laser, passes through the remote beam expanding and focusing module 7 and the reflecting mirrors, realizes coaxiality with the remote signal collecting module 11, and focuses on the liquid metal surface 23 to generate the plasma; the appearance of the position of a focus point and the condition of the generated plasma are observed in real time through the real-time imaging module 12; and after passing through the remote signal collecting module 11, the generated plasma signal light passes through the optical fiber coupling module 13 and the optical fiber 21 and enters the optical fiber spectrometer 14 to finish the collection of plasma spectral signals.

The head of the front-end high-temperature resistant probe 18 is placed in the metallurgical liquid metal 22; a sealed space is formed internally; inert gas is charged to realize an optical path environment of the inert gas; and no optical element exists in the front-end high-temperature resistant probe 18 so that it is easy to replace. The front-end high-temperature resistant probe comprises an external fireproof material part and an air charging part; the head thereof has an open structure and the tail thereof is connected with the middle-end optical sensing device; when the front-end high-temperature resistant probe is inserted into the metallurgical liquid metal, a sealed cavity body is formed therein; and the inert gas is charged therein through the air charging part to form an inert gas space so that optical paths of the excitation laser and the collected plasma light are in the inert gas environment.

The middle-end optical sensing device 19 realizes the functions of long-distance plasma excitation and signal light collection through a telescope structure, and achieves that the excitation optical path and the collection optical path are coaxial; the detection distance can be adjusted according to needs; automatic focusing can be performed; a remote laser-induced breakdown spectral sensing device with the function of real-time observation of the surface morphology of the detected substance comprises a laser generating module 6, a remote beam expanding and focusing module 7, a remote signal collecting module 11, a coaxial adjusting part (a first reflecting mirror 9 and a second reflecting mirror 10), a laser distance measuring module 8, a real-time imaging module 12 and a spectrum collecting part; and the space of the excitation and the collection optical paths is the inert gas environment formed by the front-end high-temperature resistant probe.

The laser generating module 6 in the middle-end optical sensing device generates a single laser beam or double coaxial laser beams by receiving a laser generating signal of the back-end control platform; the emergent direction of the light beam is the axis direction of the remote beam expanding and focusing module 7; and after passing through the remote beam expanding and focusing module 7, the laser is incident into a coaxial adjusting part and passes through the coaxial adjusting part to achieve that the optical axis of an excitation optical path and the optical axis of the remote signal collecting module 11 are coaxial so that the laser focuses on the measured liquid metal surface 23 through the optical path environment of the inert gas of the front-end high-temperature resistant probe 18 to form the plasma. The laser emitted by the laser distance measuring module 8 and the excitation laser which is emergent from the remote beam expanding and focusing module 7 are incident into the coaxial adjusting part in a direction of 90°, pass through the coaxial adjusting part, achieve coaxiality with the optical path of the excitation laser and the remote signal collecting module 11, and are emitted to the liquid metal surface 23. The generated plasma signals enter the remote signal collecting module 11 through the optical path environment of the inert gas of the front-end high-temperature resistant probe 18. After passing through the remote signal collecting module 11, the plasma signals pass through the light splitting piece 20. A part of plasma signal light is incident into the real-time imaging module 12 to realize the real-time monitoring of the surface appearance of a detection point, and the rest part of light is incident into the spectrum collecting part to realize the collection of the plasma signal light. The light splitting piece 20 forms an angle of 45° with the direction of the optical axis of the remote signal collecting module 11. The overall middle-end optical sensing device 19 is a constant-temperature sealed box body, and has an optical window 15 in the coaxial optical path direction.

A temperature control module 5 is connected with the back-end control platform 24 through a signal line 25, and consists of a temperature sensor and a temperature adjusting device for real-time monitoring and adjustment of the internal temperature of the middle-end optical sensing device 19 so that the internal temperature is kept within a needed temperature range.

The real-time imaging module 12 receives a part of signal light and scene background light reflected by the light splitting piece 20, feeds the same back to the back-end control platform 24, displays the appearance of the liquid metal surface 23 and the formation condition of the plasma in real time, and adjusts the focusing and collection positions according to the practical situation in real time in more detail.

The spectrum collecting part comprises an optical fiber coupling module 13, an optical fiber 21 and a spectrometer 14. The optical fiber coupling module 13 is placed on the optical axis of the plasma signal light that has passed through the light splitting piece 20, and the optical fiber 21 is connected with the optical fiber coupling module 13 and the optical fiber spectrometer 14. The signal light that has passed through the light splitting piece 20 is incident on the optical axis of the optical fiber coupling module 13 and passes through the optical fiber coupling module 13 so that the signal light is coupled into the optical fiber 21, followed by entry into the spectrometer 14 to realize the collection of the signal light.

The spectrum collecting part can also directly consist of an optical coupling system and a grating spectrometer; the optical coupling system is placed on the optical axis of the plasma signal light that has passed through the light splitting piece; and after passing through the optical coupling system, the signal light enters the grating spectrometer to realize the collection of the signal light.

Figure 2:
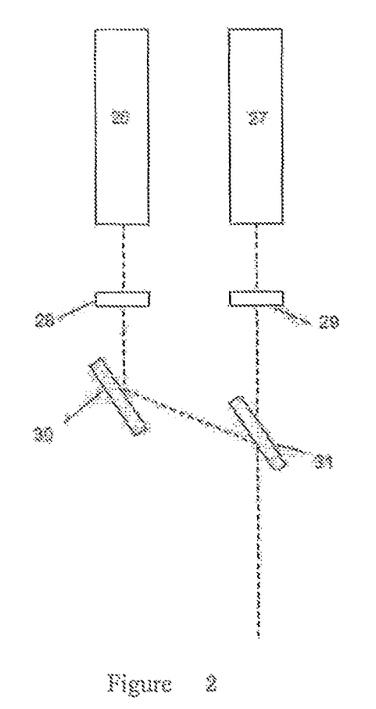
FIG. 2 is a structural diagram of a laser generating module in the present invention.

FIG. 2 shows a structural diagram of a laser generating module 6 in the present invention. The laser generating module 6 comprises a laser generating and beam combining part that comprises a first laser head 26, a second laser head 27, a first half-wave plate 28, a second half-wave plate 29, a first polarizing light splitting piece 30 and a second polarizing light splitting piece 31, wherein the first half-wave plate 28 and the first polarizing light splitting piece 30 are placed in sequence in the incident direction of the laser emitted by the first laser head 26, and respectively form a vertical angle and a Brewster's angle with the direction of the light ray of the laser; the second half-wave plate 29 and the second polarizing light splitting piece 31 are placed in the incident direction of the laser emitted by the second laser head 27, and respectively form a vertical angle and a Brewster's angle with the direction of the light ray of the laser; the pulse laser emitted by the first laser head 26 is reflected to the second polarizing light splitting piece 31 by the first polarizing light splitting piece 30, and is emitted to the direction of the optical axis of the remote focusing part after the pulse laser passes through the second polarizing light splitting piece 31; the pulse laser emitted by the second laser head 27 is emitted to the direction of the optical axis of the remote focusing part through the second half-wave plate 29 and the second polarizing light splitting piece 31; and the beam combination function is realized.

Through the double-pulse beam combination manner, the plasma excitation of double-pulse laser on the samples is realized, thereby enhancing the intensity of plasma signals and reducing the noise; and relative to a single-pulse excitation manner, the detection precision and stability can be greatly enhanced.

If single-beam laser generation is required to be realized, the first laser head 26, the first half-wave plate 28, the second half-wave plate 29, the first polarizing light splitting piece 30 and the second polarizing light splitting piece 31 can be removed; only the second laser head 27 is reserved; and the emergent direction of the laser is the direction of the optical axis of the remote beam expanding and focusing module 7.

The beam combination function of the first polarizing light splitting piece 30 and the second polarizing light splitting piece 31 can also be realized through the combination of the reflecting mirrors and a polarizing beam splitting prism.

Figure 3:
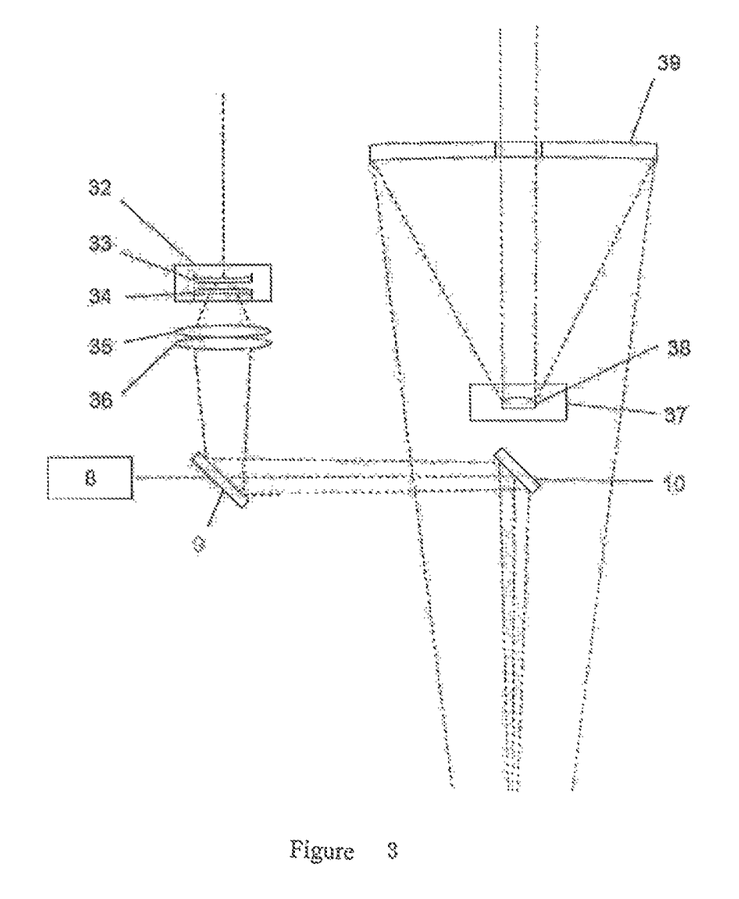
FIG. 3 is a structural diagram of a remote beam expanding and focusing module and a remote signal collecting module in the present invention.

FIG. 3 shows a structural diagram of a remote beam expanding and focusing module 7 and a remote signal collecting module 11 in the present invention. The remote beam expanding and focusing module 7 comprises a first diverging lens 33, a second diverging lens 34, a first converging lens 35, a second converging lens 36 and a first movable base 32. The first diverging lens, the second diverging lens 34 and the first converging lens 35 are coaxial with the second converging lens 36, and the first diverging lens 33 and the second diverging lens 34 are placed on the first movable base 32. The first movable base 32 can move in the direction of the optical axis of the remote beam expanding and focusing module. The coaxial adjusting part comprises a first reflecting mirror 9 and a second reflecting mirror 10, wherein the first reflecting mirror 9 is placed on the optical axis of the remote beam expanding and focusing module 7 and forms 45° with the direction of the optical axis thereof; the second reflecting mirror 10 is placed on the optical axis of the remote signal collecting module 11 and forms 45° with the optical axis thereof; and a connecting line of the centers of the first reflecting mirror 9 and the second reflecting mirror 10 is perpendicular to the directions of the optical axes of the remote beam expanding and focusing module 7 and the remote signal collecting module 11. After passing through the first reflecting mirror 9 and the second reflecting mirror 10, the excitation laser realizes coaxiality with the remote collecting module. The first reflecting mirror 9 is a reflecting mirror having a hole in the center or a laser dichroic mirror. The direction of the distance measuring laser emitted by the laser distance measuring part 8 forms 90° with the direction of the optical axis of the remote beam expanding and focusing module 7, and the distance measuring laser is incident on the center of the first reflecting mirror 9 of the coaxial adjusting part. The remote signal collecting module consists of a hyperboloidal reflecting mirror 38, a paraboloidal reflecting mirror 39 and a second movable base 37. The hyperboloidal reflecting mirror 38 is coaxial with the paraboloidal reflecting mirror 39, namely that the axial direction thereof is the axial direction of the remote signal collecting module 11; and the hyperboloidal reflecting mirror 38 is placed on the second movable base 37. The second movable base 37 can move in the direction of the optical axis, and the collection of optical signals in different focal positions is realized by adjusting the position of the second movable base 37 in the direction of the optical axis. The plasma signal light passes through the inert gas environment of the front-end high-temperature probe, and passes through the paraboloidal reflecting mirror 39 and the hyperboloidal reflecting mirror 38 to form parallel beams.

The first movable base 32 can move in the direction of the optical axis of the remote beam expanding and focusing module 7; and the continuous adjustment of the focus position of the pulse laser within the scope above 1.5 to 10 meters can be realized by adjusting the position of the first movable base 32 in the direction of the optical axis and performing focusing adjustment.

With respect to the composition of the lenses, 3 to 10 lenses can also exist to realize a remote beam expanding and focusing function.

The coaxial adjusting part comprises a first reflecting mirror 9 and a second reflecting mirror 10, wherein the first reflecting mirror 9 is placed on the optical axis of the remote beam expanding and focusing module 7 and forms 45° with the direction of the optical axis thereof; the second reflecting mirror 10 is placed on the optical axis of the remote signal collecting module 11 and forms 45° with the optical axis thereof; and a connecting line of the centers of the first reflecting mirror 9 and the second reflecting mirror 10 is perpendicular to the axes of the remote beam expanding and focusing module 7 and the remote signal collecting module 11. After passing through the first reflecting mirror 9 and the second reflecting mirror 10, the excitation laser realizes coaxiality with the remote collecting module.

The first reflecting mirror 9 is a laser dichroic mirror or a reflecting mirror having an opening in the center. If there is no laser distance measuring system 8, the reflecting mirror can be an ordinary optical reflecting mirror.

The direction of the distance measuring laser emitted by the laser distance measuring part 8 forms 90° with the direction of the optical axis of the remote beam expanding and focusing module 7, and the distance measuring laser is incident on the center of the reflecting mirror 9 of the coaxial adjusting part along the connecting line of the centers of the first reflecting mirror 9 and the second reflecting mirror 10. After passing through the second reflecting mirror 10, the distance measuring laser realizes coaxiality with the optical path of the plasma excitation beam and the optical path of the remote signal collecting module 11 and is emitted to the liquid metal surface. Distance measuring signal light thereof returns to a laser distance measuring instrument according to an original optical path to realize a laser distance measuring function.

The second movable base 37 can move in the direction of the optical axis, and the collection of optical signals in different focal positions is realized by adjusting the position of the second movable base 37 in the direction of the optical axis and performing focusing adjustment.

The hyperboloidal reflecting mirror 38 and the paraboloidal reflecting mirror 39 can also consist of a group of spherical reflecting mirror and aspherical reflecting mirror.

Figure 4:
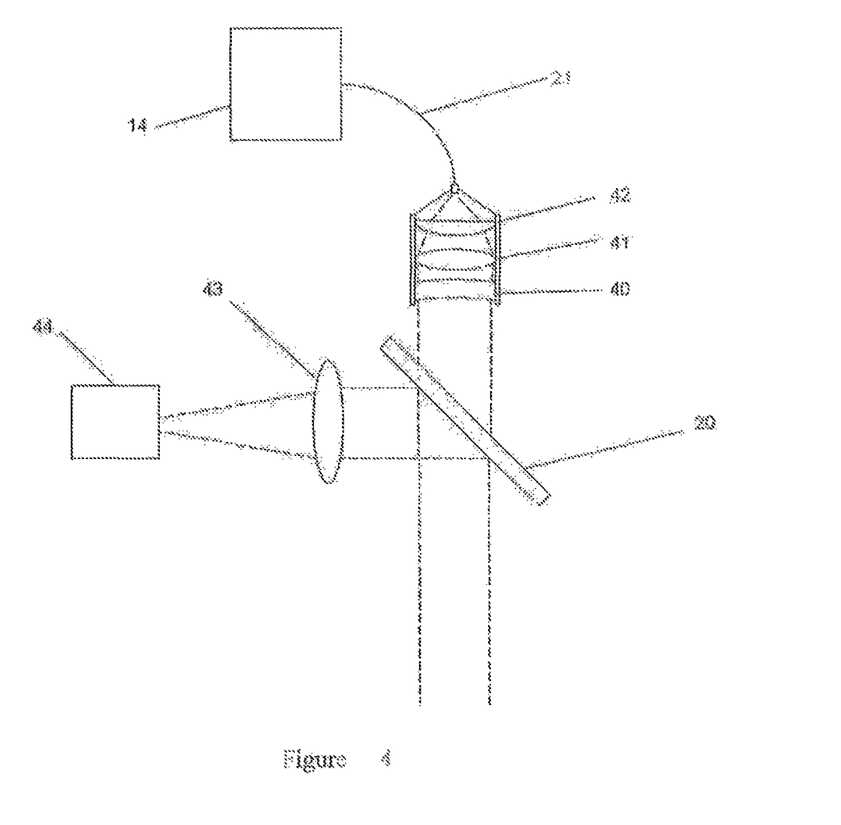
FIG. 4 is a structural diagram of a real-time imaging module and an optical fiber coupling module in the present invention.

FIG. 4 shows a structural diagram of a real-time imaging part 12 and an optical fiber coupling module 13 in the present invention. The optical fiber coupling module 13 consists of a third diverging lens 40, a third converging lens 41 and a fourth converging lens 42 which are coaxially placed in parallel, and the optical axis of the optical fiber coupling module 13 coincides with the optical axis of the remote signal collecting module.

The real-time imaging module 12 comprises an achromatic lens 43 and a CCD 44. The achromatic lens 43 and the CCD 44 are coaxially placed; the axis direction thereof is perpendicular to the direction of the optical axis of the remote signal collecting module 11; and the axis passes through the center of the light splitting piece 20.

The front-end high-temperature resistant probe 18 and the middle-end optical sensing device are integrated into a whole and are installed on a hydraulic platform which can move in a perpendicular direction.

The back-end control platform as a platform of manual control, operation and display is placed in a control room, is connected with the middle-end optical sensing device through a signal line for controlling a laser signal of the middle-end optical sensing device, controls the movement of displacement platforms and the like in the remote beam expanding and focusing module 7 and the remote signal collecting module 11 through the information of the laser distance measuring part and the real-time imaging part, receives electrical signals, which can be transmitted in long distance, transmitted by the middle-end optical sensing device for processing, and controls the gas flow of the front-end high-temperature resistant probe 18.

The back-end control platform of the present invention partially controls the laser distance measuring part for performing the distance measurement of the liquid metal surface, adjusts the detection distance and the collection distance according to measured information, performs focusing adjustment, controls the generation of the laser signal and the collection of detection signals, controls air charging flow, displays the surface morphology information of the detection point and the generation condition of the plasma in real time, simultaneously processes and analyzes the detection data and provides manual operation and display functions. A time synchronization controller controls the emission time delay of two laser pulse beams and the collection time of the detection signals of the spectrometer. The signal-to-noise ratio of the spectral signals can be increased by optimizing the time delay between the two laser beams and the signal collection time of the spectrometer. The detection signals of the spectrometer are transmitted into a computer; and the processing courses of denoising, background elimination, peak searching and the like are performed on the data in the computer to obtain the strength of the characteristic spectral line of a measured component. The concentration of the measured component can be computed through the strength of the characteristic spectral line and an established strength-concentration calibration curve.

Focusing adjustment has the following steps:

setting a distance from the laser distance measuring module 8 to the center of the second reflecting mirror 10 as 1, a constant value, setting a distance from the second reflecting mirror 10 to the measured liquid metal surface 23 as s to obtain the measurement value of the laser distance measuring module 8: $a=1+s$;

enabling the first movable base 32 to be within the movement scope itself; enabling a movement position value x1 and a position value s1 for focusing the laser to form a monotone function that corresponds to a unique determined value; and setting a corresponding relationship therebetween to be $x1=f1(s1)$, while representing s1 as an addition form of s and a constant offset 11, i.e., $s1=s+11$ to obtain $x1=f1(s+11)$;

enabling the second movable base 37 to be within the movement scope itself; enabling a movement position value x2 and a position value s2 of the collection position of the signal light to form a monotone function that corresponds to a unique determined value; and setting a corresponding relationship therebetween to be $x2=f2(s2)$, while representing s2 as an addition form of s and a constant offset 12, i.e., $s2=s+12$ to obtain $x2=f2(s+12)$; and calibrating the functions $x1=f1(s+11)$ and $x2=f2(s+12)$ to obtain the values of x1 and x2 through the known s so as to obtain the position values x1 and x2 for the movement of the first movable base 32 the second movable base 37 through a value obtained by laser distance measurement, thereby realizing focusing adjustment.

Through the above-mentioned method and steps, an automatic focusing function can be realized, namely that the laser focusing position of the remote beam expanding and focusing module 7 and the signal collection position of the remote signal collecting module 11 are automatically adjusted through a measurement feedback signal of the laser distance measuring module 8 so that the laser focusing position and the signal collection position coincide on the liquid metal surface 23 to be measured.

The device of the present invention not only can realize in-situ detection, but also can realize online detection. The difference between in-situ and online is that in-situ detection means detection without disassembling original equipment and interfering with an original production process, and emphasizes spatiality; and online detection means instantaneous detection on a detection object on a production line and emphasizes timeliness. Through the adoption of the device of the present invention, instantaneous and quick detection without interfering with the production process can be realized.

By taking the detection of metallurgical liquid steel as an example, the working process of the device of the present invention is as follows:

Firstly, the front-end high-temperature resistant optical probe 18 is slowly extended into a melt (metallurgical liquid metal 22) through an elevating mechanism, and an air charging pipe 16 and an air charging pipe 17 open the gas flow of 30 L/min to form an optical path environment of the inert gas. When the front-end high-temperature resistant optical probe 18 is inserted into a level depth between 20 cm to 30 cm, the position thereof is fixed; the laser distance measuring part 18 starts to work and emits distance measuring laser; and the position to be measured of the metallurgical liquid metal surface 23 in the high-temperature resistant probe 18 is measured and fed back to the back-end control platform.

The back-end control platform performs position adjustment on the first movable base 32 and the second movable base 37 in the remote beam expanding and focusing module 7 and the remote signal collecting module 11 through the distance position measured by the laser distance measuring part so that the focusing position of the measurement laser and the collection position of remote signals are identical and are on the metallurgical liquid metal surface 23.

After the position adjustment is finished, the first laser head 26 and the second laser head 27 receive the signals of the back-end control platform and emit the laser. The laser emitted by the first laser head 26 passes through the first half-wave plate 28, the first polarizing light splitting piece 30 and the second polarizing light splitting piece 31, and is incident into the remote beam expanding and focusing module 7 in the direction of the optical axis of the remote beam expanding and focusing module 7. The laser emitted by the second laser head 27 passes through the second half-wave plate 29 and the second polarizing light splitting piece 31 to realize beam combination with the laser emitted by the first laser head 26, and is likewise incident into the remote beam expanding and focusing module 7 in the direction of the optical axis of the remote beam expanding and focusing module 7.

Two laser beams after the beam combination pass through the remote beam expanding and focusing module 7 to form a wide focusing beam with a larger diameter; and the wide focusing beam is incident on the first reflecting mirror 9 of the coaxial adjusting part. The first reflecting mirror 9 is placed in the direction of the optical axis of the remote beam expanding and focusing module 7 and forms 45° with the optical axis of the remote beam expanding and focusing module 7. The laser that has passed through the first reflecting mirror 9 is reflected to the second reflecting mirror 10. The second reflecting mirror 10 is placed in the direction of the optical axis of the remote signal collecting module 11 and forms 45° with the optical axis of the remote signal collecting module 11. Moreover, a connecting line of the centers of the first reflecting mirror 9 and the second reflecting mirror 10 is perpendicular to the directions of the optical axes of the remote beam expanding and focusing module 7 and the remote signal collecting module 11. The second reflecting mirror 10 reflects the two focusing laser beams to the direction of the optical axis of the remote signal collecting module 11 to realize coaxiality between the excitation optical path and the collection optical path.

The two laser beams after the beam combination are made to pass through the second reflecting mirror 10 and an optical window 15 and to focus on the metallurgical liquid metal surface 23, so as to form the plasma. After passing through the optical window 15, the light ray emitted by the plasma is incident into the remote signal collecting module 11, and in the remote signal collecting module 11, passes through the paraboloidal reflecting mirror 39 and the hyperboloidal reflecting mirror 38 to form parallel beams.

The light splitting piece 20 is placed in the direction of the optical axis of the remote signal collecting module 11 and forms 45° with the optical axis. After passing through the light splitting piece 20, the parallel signal light is partially reflected to a real-time display system 12; the surface appearance of a sampling point and the formation condition of the plasma can be observed in real time and fed back to the back-end control platform; the focusing position can be adjusted slightly; and the rest part of the parallel signal light is incident into the optical fiber coupling module 13 that is likewise placed in the direction of the optical axis of the remote signal collecting module 11, and enters the spectrometer 14 after passing through the optical fiber 21 to finish the collection of the plasma signal light.

The spectrometer performs light splitting and photoelectric conversion on the collected plasma emission light rays, and transmits converted electrical signals to a console through a cable to perform data analysis and processing. The middle-end optical sensing device 19 is a constant-temperature box body, and the temperature is controlled below 30° C.

The invention claimed is:

1. An in-situ online detection device for a long-distance metallurgical liquid metal component, comprising:
   a front-end high-temperature resistant probe that comprises a head designed for placement in liquid metal, said probe further comprising a tail section;
   a middle-end optical sensing device connected to the tail section and comprising a remote signal collecting module;
   an optical window provided at an interface region of the tail section and middle-end optical sensing device;
   a laser generating module;
   a back-end control platform; and wherein
   the tail section is coaxially connected to the middle-end optical sensing device, and the middle-end optical sensing device is connected to the back-end control platform through a signal line, and
   said middle-end optical sensing device comprises a remote beam expanding and focusing module that is arranged coaxially in an axis direction in which the laser generating module emits one or more laser beams; and
   a first laser beam reflecting mirror is arranged on an optical axis of an emergent direction of the remote beam expanding and focusing module and forms an angle of 45° with the optical axis thereof;
   a second laser beam reflecting mirror is arranged on an optical axis of an incident direction of the remote signal collecting module and forms an angle of 45° with the optical axis thereof; and
   a connecting line of the centers of the first laser beam reflecting mirror and the second laser beam reflecting mirror is perpendicular to the axes of the optical axis of the emergent direction of the remote beam expanding and focusing module and the optical axis of the incident axis direction of the remote signal collecting module;
   said remote beam expanding and focusing module comprises a first movable base and a diverging lens and a converging lens which are coaxially arranged on the optical axis of the emergent direction of the laser generating module;
   said first movable base being adjustable on the optical axis of the emergent direction of the laser generating module;
   said diverging lens being arranged in the first movable base perpendicular to the optical axis of the emergent direction of the laser generating module; and
   said converging lens being arranged between the first movable base and the first laser beam reflecting mirror and perpendicular to the optical axis of the emergent direction of the laser generating module.

2. The in-situ online detection device for the long-distance metallurgical liquid metal component according to claim 1, wherein:
said middle-end optical sensing device further comprises
a light splitting piece and an optical fiber coupling module that are respectively arranged on the optical axis of an emergent direction of the remote signal collecting module; the optical fiber coupling module is connected with an optical fiber spectrometer through an optical fiber; and the fiber spectrometer is connected with the back-end control platform through the signal line; and
a real-time imaging module is vertically arranged on an optical axis of a reflecting direction of the light splitting piece, and is connected with the back-end control platform through the signal line.

3. The in-situ online detection device for the long-distance metallurgical liquid metal component according to claim 2, wherein said remote signal collecting module further comprises a second movable base, a hyperboloidal reflecting minor and a paraboloidal reflecting mirror;
said second movable base is adjustable on the optical axis of an emergent direction of the second laser beam reflecting mirror;
said hyperboloidal reflecting minor is coaxial with the optical axis of the emergent direction of the second laser beam reflecting mirror, and is arranged in the second movable base; and
said paraboloidal reflecting minor is arranged between the hyperboloidal reflecting mirror and the light splitting piece, and a central hole is reserved in the center of said paraboloidal reflecting mirror.

4. The in-situ online detection device for the long-distance metallurgical liquid metal component according to claim 2, wherein said optical fiber coupling module comprises a third diverging lens, a third converging lens and a fourth converging lens which are coaxially placed in parallel in sequence, and the optical axis thereof coincides with the optical axis of the remote signal collecting module.

5. The in-situ online detection device for the long-distance metallurgical liquid metal component according to claim 2, wherein said real-time imaging module comprises an achromatic lens and a CCD; and the achromatic lens and the CCD are coaxially placed on an axis direction that is perpendicular to the optical axis of the emergent direction of the remote signal collecting module; and the axis passes through the center of the light splitting piece.

6. The in-situ online detection device for the long-distance metallurgical liquid metal component according to claim 2, wherein: said back-end control platform comprises a laser power supply and control unit, a time synchronization controller, an air inlet control unit and a displacement platform control unit, wherein the above-mentioned units are connected with the middle-end optical sensing device through the signal line.

7. The in-situ online detection device for the long-distance metallurgical liquid metal component according to claim 2, wherein said laser generating module comprises two groups of laser heads, half-wave plates and polarizing light splitting pieces;
said half-wave plates are coaxially arranged on the optical axes of the laser emergent directions of the laser heads and are perpendicular to the optical axes; and
said polarizing light splitting pieces are coaxially arranged on the optical axes of the emergent directions of the half-wave plates and form Brewster's angles with the optical axes, and the second polarizing light splitting piece can receive the laser beams reflected by the first polarizing light splitting piece.

8. The in-situ online detection device for the long-distance metallurgical liquid metal component according to claim 1, wherein: said front-end high-temperature resistant probe is an inverted cone in which inert gas is charged so that an, optical path of an excitation laser beam generated by the laser generating module and a collected plasma signal light are in a closed inert gas environment.

9. The in-situ online detection device for the long-distance metallurgical liquid metal component according to claim 1, wherein: said back-end control platform comprises a laser power supply and control unit, a time synchronization controller, an air inlet control unit and a displacement platform control unit, wherein the above-mentioned units are connected with the middle-end optical sensing device through the signal line.

10. The in-situ online detection device for the long-distance metallurgical liquid metal component according to claim 1, further comprising a laser distance measuring module which has a distance laser arranged so as to extend in the direction of a connecting line of the centers of the first laser beam reflecting minor and the second laser beam reflecting mirror, and the laser distance measuring module is connected with the back-end control platform through the signal line.

11. The in-situ online detection device for the long-distance metallurgical liquid metal component according to claim 1, wherein said middle-end optical sensing device further comprises a temperature control module and is connected with the back-end control platform through the signal line; and said temperature control module comprises a temperature sensor and a temperature adjusting device for real-time monitoring and adjustment of the internal temperature of the middle-end optical sensing device.

12. The in-situ online detection device for the long-distance metallurgical liquid metal component according to claim 1, wherein said laser generating module comprises two groups of laser heads, half-wave plates and polarizing light splitting pieces;
said half-wave plates are coaxially arranged on respective optical axes of the laser emergent directions of the laser heads and are perpendicular to said respective optical axes; and
said polarizing light splitting pieces are coaxially arranged on respective optical axes of the emergent directions of the half-wave plates and form Brewster's angles with the said respective optical axes, and the second polarizing light splitting piece is positioned to receive laser beams reflected by the first polarizing light splitting piece.

13. The in-situ online detection device for the long-distance metallurgical liquid metal component according to claim 1, further comprising a light splitting piece and wherein said remote signal collecting module comprises a second movable base, a spherical reflecting mirror and an aspherical reflecting mirror and is connected with the back-end control platform through the signal line;
said second movable base is adjustable on an optical axis of an emergent direction of the second laser beam reflecting mirror;
said spherical reflecting minor is parallel to and coaxial with the emergent direction of the second laser beam reflecting mirror, and is arranged in the second movable base; and
said aspherical reflecting mirror is arranged between the spherical reflecting minor and the light splitting piece, and a central hole is reserved in the center of said aspherical reflecting mirror.

14. An in-situ online detection method for a long-distance metallurgical liquid metal component, comprising the following steps:

placing a head of a front-end high-temperature resistant probe in liquid metal; and charging inert gas through an air inlet pipe of the high-temperature resistant probe to form a closed inert gas environment;

emitting a distance measuring laser by a laser distance measuring module; after the distance measuring laser passes through a first laser beam reflecting mirror and to a second laser beam reflecting mirror, irradiating the distance measuring laser on a liquid metal surface; measuring position information of the liquid metal surface; and feeding the same back to a back-end control platform;

performing focusing adjustment on a first movable base of a remote beam expanding and focusing module and a second movable base of a remote signal collecting module by the back-end control platform through use of the position information of the liquid metal surface that is fed back by the laser distance measuring module so that the focal position, on which the laser focuses, for exciting plasma from the liquid metal, and a collection position of remote signals coincide on the liquid metal surface;

receiving a laser generating signal of the back-end control platform by a laser generating module; emitting at least one laser beam; after the at least one laser beam passes through the remote beam expanding and focusing module, irradiating the at least one laser beam on the first laser beam reflecting mirror; enabling the at least one laser beam, reflected off the first laser beam reflecting mirror, to reflect off the second laser beam reflecting mirror to the liquid metal surface through the inert gas environment of the front-end high-temperature resistant probe to produce plasma signal light;

transmitting the generated plasma signal light to the remote signal collecting module through the inert gas environment of the front-end high-temperature resistant probe;

forming parallel plasma signal light through a paraboloidal reflecting mirror and a hyperboloidal reflecting mirror in the remote signal collecting module; and transmitting the same to an optical fiber coupling module through a light splitting piece; and further transmitting the parallel plasma signal light that passes through the optical fiber coupling module through an optical fiber end to an optical fiber spectrometer for performing light signal collection and photoelectric conversion; and feeding photoelectric conversion data to the back-end control platform.

15. The in-situ online detection method for the long-distance metallurgical liquid metal component according to claim 14, further comprising utilizing a real-time imaging module which receives a part of signal light and scene background light reflected by the light splitting piece, feeds the same back to the back-end control platform, displays the appearance of the liquid metal surface and the formation condition of the plasma in real time, and adjusts the focusing position and the collection position in real time.

* * * * *